(12) United States Patent
Sundler et al.

(10) Patent No.: US 10,792,473 B2
(45) Date of Patent: Oct. 6, 2020

(54) CORE WIRE HAVING A FLATTENED PORTION TO PROVIDE PREFERENTIAL BENDING

(71) Applicant: ST. JUDE MEDICAL COORDINATION CENTER BVBA, Zaventem (BE)

(72) Inventors: Sara Sundler, Uppsala (SE); Michael S. Morrissey, St. Paul, MN (US)

(73) Assignee: ST. JUDE MEDICAL COORDINATION CENTER BVBA, Zaventem (BE)

(*) Notice: Subject to any disclaimer, the term of this patent is extended or adjusted under 35 U.S.C. 154(b) by 343 days.

(21) Appl. No.: 15/072,021

(22) Filed: Mar. 16, 2016

(65) Prior Publication Data

US 2017/0266417 A1  Sep. 21, 2017

(51) Int. Cl.
| | |
|---|---|
| *A61M 25/09* | (2006.01) |
| *A61B 5/00* | (2006.01) |
| *A61B 5/02* | (2006.01) |
| *A61B 5/026* | (2006.01) |

(52) U.S. Cl.
CPC .......... *A61M 25/09* (2013.01); *A61B 5/6851* (2013.01); *A61B 5/026* (2013.01); *A61B 5/02007* (2013.01); *A61M 2025/09066* (2013.01); *A61M 2025/09075* (2013.01); *A61M 2025/09083* (2013.01); *A61M 2025/09108* (2013.01); *A61M 2025/09133* (2013.01); *A61M 2025/09175* (2013.01)

(58) Field of Classification Search
CPC .................................................... A61M 25/09
USPC ........................................................ 600/585
See application file for complete search history.

(56) References Cited

U.S. PATENT DOCUMENTS

| | | | |
|---|---|---|---|
| 4,854,330 A * | 8/1989 | Evans, III | A61M 25/09 600/585 |
| RE35,648 E | 11/1997 | Tenerz et al. | |
| 5,707,354 A | 1/1998 | Salmon et al. | |
| 5,730,717 A | 3/1998 | Gelbfish | |
| 5,836,893 A | 11/1998 | Urick | |
| 5,951,480 A | 9/1999 | White et al. | |
| 5,957,865 A | 9/1999 | Backman et al. | |

(Continued)

FOREIGN PATENT DOCUMENTS

| | | |
|---|---|---|
| EP | 1 475 036 B1 | 11/2004 |
| EP | 1 479 407 B1 | 11/2004 |

(Continued)

OTHER PUBLICATIONS

Japanese Office Action and English language translation, dated Dec. 2, 2014, 7 pages.

(Continued)

*Primary Examiner* — Daniel L Cerioni
*Assistant Examiner* — Raymond P Dulman
(74) *Attorney, Agent, or Firm* — Foley & Lardner LLP (57) ABSTRACT

A guide wire configured for intravascular insertion includes a core wire having a flattened portion configured to allow the core wire to preferentially bend in at least one plane that passes through a longitudinal axis of the core wire. A distal most end of the flattened portion is spaced from a distal most end of the core wire. The guide wire may further include a sensor element configured to measure a physiological variable in a living body and a coil surrounding a portion of the core wire.

25 Claims, 9 Drawing Sheets

(56) References Cited

U.S. PATENT DOCUMENTS

| | | | |
|---|---|---|---|
| 6,167,763 B1 | 1/2001 | Tenerz et al. | |
| 6,190,332 B1 | 2/2001 | Muni et al. | |
| RE37,148 E | 4/2001 | Shank | |
| 6,261,246 B1 | 7/2001 | Pantages et al. | |
| 6,290,656 B1* | 9/2001 | Boyle | A61M 25/09 600/585 |
| 6,352,515 B1* | 3/2002 | Anderson | A61M 25/09 600/585 |
| 6,464,699 B1 | 10/2002 | Swanson | |
| 6,464,700 B1 | 10/2002 | Koblish et al. | |
| 6,692,491 B1 | 2/2004 | Phan | |
| 6,866,642 B2 | 3/2005 | Kellerman et al. | |
| 7,052,473 B2 | 5/2006 | Hill | |
| 7,115,101 B2 | 10/2006 | Cornelius et al. | |
| 7,169,118 B2 | 1/2007 | Reynolds et al. | |
| 7,175,619 B2 | 2/2007 | Koblish et al. | |
| 7,214,201 B2 | 5/2007 | Burmeister et al. | |
| 7,399,283 B2 | 7/2008 | Kato | |
| 7,455,646 B2 | 11/2008 | Richardson et al. | |
| 7,724,148 B2 | 5/2010 | Samuelsson et al. | |
| 7,789,839 B2 | 9/2010 | Lupton | |
| 7,942,832 B2 | 5/2011 | Kanuka et al. | |
| 8,075,497 B2 | 12/2011 | Melsheimer | |
| 8,105,246 B2 | 1/2012 | Voeller et al. | |
| 8,133,190 B2 | 3/2012 | Melsheimer et al. | |
| 8,174,395 B2 | 5/2012 | Samuelsson et al. | |
| 8,222,566 B2 | 7/2012 | Shireman et al. | |
| 8,257,278 B2 | 9/2012 | Howland et al. | |
| 8,277,386 B2 | 10/2012 | Ahmed et al. | |
| 8,360,995 B2 | 1/2013 | Elsesser et al. | |
| 8,419,658 B2 | 4/2013 | Eskuri | |
| 8,460,213 B2 | 6/2013 | Northrop | |
| 8,461,997 B2 | 6/2013 | Samuelsson et al. | |
| 8,602,974 B2 | 12/2013 | Goldwasser et al. | |
| 8,608,670 B2 | 12/2013 | Matsumoto et al. | |
| 8,608,703 B2 | 12/2013 | Riles et al. | |
| 8,698,638 B2 | 4/2014 | Samuelsson et al. | |
| 8,758,269 B2 | 6/2014 | Miyata et al. | |
| 8,784,337 B2 | 7/2014 | Voeller et al. | |
| 8,845,551 B2 | 9/2014 | Kato | |
| 9,028,427 B2 | 5/2015 | Kinoshita et al. | |
| 9,095,685 B2* | 8/2015 | Sela | A61B 5/06 |
| 9,155,492 B2 | 10/2015 | Jenkins et al. | |
| 2002/0019626 A1 | 2/2002 | Sharkey et al. | |
| 2002/0032390 A1* | 3/2002 | Jafari | A61M 25/09 600/585 |
| 2002/0188189 A1 | 12/2002 | Belef et al. | |
| 2004/0167436 A1 | 8/2004 | Reynolds et al. | |
| 2004/0167438 A1 | 8/2004 | Sharrow | |
| 2004/0193034 A1 | 9/2004 | Wasicek et al. | |
| 2006/0074318 A1 | 4/2006 | Ahmed et al. | |
| 2006/0116571 A1 | 6/2006 | Maschke et al. | |
| 2006/0247672 A1 | 11/2006 | Vidlund et al. | |
| 2007/0167972 A1* | 7/2007 | Euteneuer | A61M 25/09 606/192 |
| 2007/0244413 A1 | 10/2007 | Biggins | |
| 2007/0255145 A1 | 11/2007 | Smith et al. | |
| 2008/0119762 A1 | 5/2008 | Tateishi et al. | |
| 2008/0306468 A1* | 12/2008 | Tamai | A61M 25/09 604/528 |
| 2009/0062602 A1 | 3/2009 | Rosenberg et al. | |
| 2009/0088650 A1 | 4/2009 | Corl | |
| 2009/0192412 A1 | 7/2009 | Sela et al. | |
| 2009/0192413 A1 | 7/2009 | Sela et al. | |
| 2009/0198153 A1 | 8/2009 | Shriver | |
| 2009/0227902 A1 | 9/2009 | Simpson et al. | |
| 2009/0254000 A1 | 10/2009 | Layman et al. | |
| 2010/0030113 A1 | 2/2010 | Morriss et al. | |
| 2010/0222637 A1 | 9/2010 | Kassab | |
| 2010/0228112 A1 | 9/2010 | Von Malmborg | |
| 2011/0098648 A1 | 4/2011 | Kato | |
| 2011/0213220 A1 | 9/2011 | Samuelsson et al. | |
| 2012/0041342 A1 | 2/2012 | Purtzer | |
| 2012/0289808 A1 | 11/2012 | Hubinette | |
| 2013/0172782 A1 | 7/2013 | Hilmersson | |
| 2013/0237864 A1 | 9/2013 | Mazar et al. | |
| 2014/0005543 A1 | 1/2014 | Burkett | |
| 2014/0066790 A1 | 3/2014 | Burkett et al. | |
| 2014/0066791 A1 | 3/2014 | Burkett | |
| 2014/0180141 A1 | 6/2014 | Millett | |
| 2014/0180166 A1* | 6/2014 | Isch | A61M 25/09 600/585 |
| 2014/0187978 A1 | 7/2014 | Millett et al. | |
| 2014/0187979 A1 | 7/2014 | Burkett | |
| 2015/0094616 A1* | 4/2015 | Simpson | A61M 25/09 600/585 |
| 2016/0022215 A1* | 1/2016 | Henderson | A61B 5/6851 600/486 |

FOREIGN PATENT DOCUMENTS

| | | |
|---|---|---|
| EP | 1 267 737 B1 | 10/2005 |
| EP | 1 616 521 A1 | 1/2006 |
| EP | 2 481 440 A1 | 8/2012 |
| JP | 2002-538854 A | 11/2002 |
| JP | 2006-026406 A | 2/2006 |
| JP | 2006-519062 A | 8/2006 |
| JP | 3876080 B2 | 1/2007 |
| JP | 2009-172385 A | 8/2009 |
| JP | 2010-187929 A | 2/2010 |
| JP | 5229830 B2 | 7/2013 |
| JP | 2014-023943 A | 2/2014 |
| JP | 5751624 B2 | 7/2015 |
| WO | WO-00/38775 A2 | 7/2000 |
| WO | WO-2004/075950 A2 | 9/2004 |
| WO | WO-2007/105531 A1 | 9/2007 |
| WO | WO-2009/054800 A1 | 4/2009 |

OTHER PUBLICATIONS

Japanese Office Action and English language translation, dated Oct. 31, 2017, 9 pages.

Japanese Office Action and English translation, dated Feb. 7, 2017, 8 pages.

Japanese Office Action and English translation, dated Aug. 30, 2016, 14 pages.

USPTO Office Action, U.S. Appl. No. 13/823,063, dated May 2, 2016, 13 pages.

USPTO Office Action, U.S. Appl. No. 13/823,063, dated Jun. 7, 2017 11 pages.

USPTO Office Action, U.S. Appl. No. 13/823,063, dated Nov. 23, 2016, 19 pages.

USPTO Office Action, U.S. Appl. No. 13/823,063, dated Dec. 6, 2017, 12 pages.

USPTO Office Action, U.S. Appl. No. 13/823,063, dated Mar. 14, 2018, 16 pages.

USPTO Office Action, U.S. Appl. No. 13/823,063, dated Oct. 15, 2018, 17 pages.

International Preliminary Report on Patentability, PCT/US2017/022514, dated Sep. 27, 2018, 7 pages.

Japanese Office Action and English translation, Application No. 2018-054871, dated Feb. 26, 2019, 8 pages.

USPTO Notice of Allowance, U.S. Appl. No. 13/823,063, dated Jan. 30, 2019, 9 pages.

European Office Action, Application No. 17714961.4, dated Jun. 25, 2019, 6 pages.

Japanese Office Action and English translation, Application No. 2018-054871, dated Aug. 6, 2019, 7 pages.

Japanese Office Action and English translation, Application No. 2018-544541, dated Jul. 2, 2019, 5 pages.

Japanese Office Action and English translation, Application No. 2018-544541, dated Jun. 9, 2020, 16 pages.

* cited by examiner

CORE WIRE HAVING A FLATTENED PORTION TO PROVIDE PREFERENTIAL BENDING

BACKGROUND

The invention generally relates to the area of medical devices. More particularly, the present invention concerns a sensor guide wire for intravascular measurements of a physiological or other variable, for example, pressure or temperature, inside a living human or animal body, the sensor guide wire including a core wire having at least a portion that is flattened.

Equipment and processes have been developed for assisting medical personnel, such as physicians, in diagnosing physiological conditions of a patient. For example, sensor guide wires in which a sensor is mounted at the distal end thereof have been developed. The sensor may be, for example, an intra-vascular pressure sensor that is arranged to measure blood pressure at various points within the vasculature to facilitate locating and determining the severity of, for example, stenosis or other disruptors of blood flow within the vessels of the living body.

Sensor and guide wire assemblies in which a sensor is mounted at the distal end of a guide wire are known. In U.S. Pat. No. Re. 35,648, which is assigned to the present assignee, an example of such a sensor guide wire is disclosed, where a sensor guide wire comprises a sensor element, an electronic unit, at least one signal transmitting cable connecting the sensor element to the electronic unit, a flexible tube having the cable disposed therein, a solid metal wire, and a coil attached to the distal end of the solid wire. The sensor element comprises a pressure sensitive device, e.g. a membrane, with piezoresistive elements connected in a Wheatstone bridge-type of arrangement mounted thereon.

The above-mentioned solid metal wire, also called the core wire, extends from the distal end of the sensor guide wire to the proximal portion, where a male connector is arranged, and determines in part the overall mechanical properties, such as flexibility, torqueability and pushability, of the sensor guide wire. Sensor and guide wire assemblies for intravascular measurements are generally long, e.g. 100-300 cm, and have a small diameter, e.g. 0.35 mm. The core wire often extends along essentially the entire length of the sensor guide wire.

A hollow tube (or proximal tube) may extend from a proximal male connector to a jacket, inside which a sensor element is arranged. As an alternative, a proximal tube may extend from a proximal male connector to a coil, which, in turn, is connected to such a jacket. The core wire is inserted through a lumen of the proximal tube. The core wire may be longer than the proximal tube, and may extend from the proximal male connector, through the jacket, and to the distal tip of the sensor guide wire.

A core wire is a wire typically made out of metal and is typically of complex mechanical construction since it has to be steered often several feet into a patient, for example, from an opening in the femoral artery in the leg of the patient up to the heart through tortuous blood vessels. The mechanical characteristics (such as maneuverability, steerability, torqueability, pushability and shapeability) of a guide wire are very important to a surgeon because the surgeon grasps the proximal end of a guide wire (sticking outside the patient), and by manipulating the proximal end, steers the distal end of the guide wire, which is often several feet away.

Maneuverability describes the overall ability of the guide wire to travel through complex anatomies and is influenced by a number of factors including flexibility, strength, torqueability, pushability and friction within the anatomical environment.

Steerability describes a guide wire's ability to react to torque and push so that the distal end reaches parts of vessels as intended by the user. Steerability is primarily determined by the guide wire's stiffness and its thickness or strength.

Torqueability describes the ability of the guide wire to transmit a rotational displacement along the length of the sensor guide wire. When the rotational movements by the physician translate exactly to the tip of the sensor guide wire within the anatomy, the torque performance is high, so called "1:1" torque ratio.

Pushability describes the ability of the guide wire to transmit a longitudinal force from the proximal end of the shaft to the distal end. When a guide wire shaft has been designed to optimize pushability, it is easier for the physician to maneuver the sensor guide wire to the desired spot.

Shapeability describes the ability of the guide wire to be shaped either during the guide wire's manufacture or by a surgeon at the time of the procedure into a desired orientation. For example, prior to inserting the guide wire into a patient, the surgeon may reshape the wire manually or by winding the wire around a needle. After reaching a first target, the guide wire may also be removed from the patient's body, reshaped, and reinserted to reach a second target. When reshaping the guide wire, the surgeon may impose, for example, a sharper angle of 30-80 degrees in an up-down direction. During shaping, the guide wire is bent or shaped into a particular angle and shape based on a particular use of the guide wire and/or the known location of the target to be treated or diagnosed and the path needed to reach the target.

The guide wire is steered through the arteries, rather than being "pushed" or simply "introduced" through the arteries. A typical guide wire is very thin (typically 0.35 mm or less in diameter). Since the artery wall is soft, any attempt to use the artery itself as a guide for the guide wire could lead to penetration of the artery wall. The guide wire must be steered, for example, from an opening in the femoral artery in the leg of the patient up to the heart through tortuous blood vessels.

General background on guide wire systems will be described first in conjunction with FIGS. 1 and 2.

Figure 1:
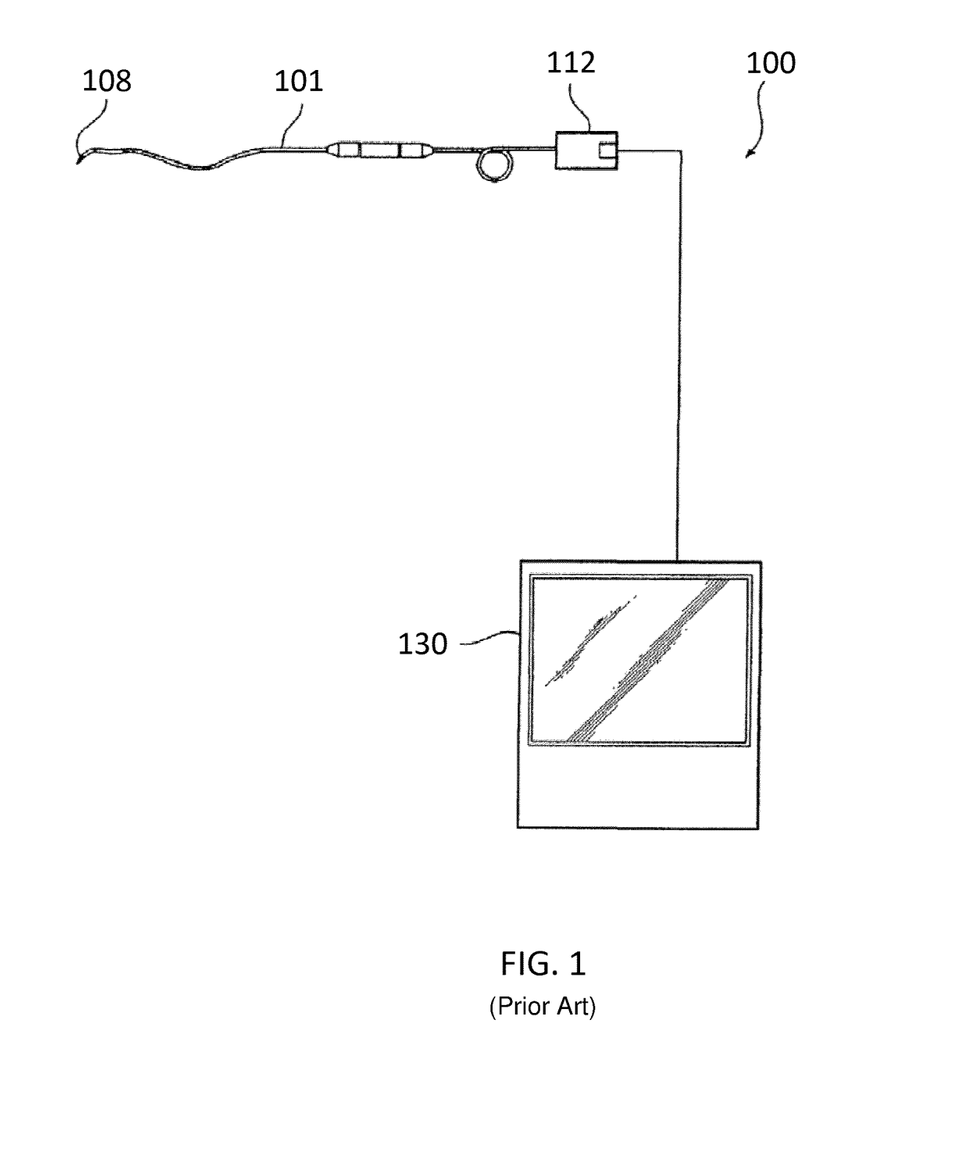
FIG. 1 is a schematic drawing showing a system for intravascular measurement.

FIG. 1 shows a system 100 comprising a sensor guide wire 101 and a physiological monitor 130. The sensor guide wire 101 may comprise a sensor element 108 arranged at the distal end of the sensor guide wire 101. The sensor element 108 may be arranged to sense a physiological or other variable in a living body, such as a human or animal body, and provide a sensor signal. The sensor guide wire 101 is a disposable device which typically includes a proximal connector 112 (which may be a female or male connector) for connection to the physiological monitor 130 which processes the sensor signal to generate a measurement of the physiological or other variable. Alternatively, a signal converting device or an interfacing device may be disposed between the proximal connector 112 and the physiological monitor 130, such as for example, the signal converting and interfacing devices disclosed in U.S. Patent Application Publication No. 2012/0289808, which is hereby incorporated by reference in its entirety for its teachings related to signal converting and interfacing devices, the use of physiological monitors, and the structure and use of sensor guide wire devices. Such a signal converting or interfacing device may be arranged to interface the sensor element 108 to the physiology monitor 130 such that a signal indicative of the physiological or other variable sensed by the sensor element 108 is pre-processed and forwarded to the physiology monitor 130. According to other embodiments, the sensor guide wire 101 can communicate via wireless transmission with the physiological monitor 130 such as, for example, the wireless transmission arrangement disclosed in U.S. Pat. Nos. 7,724,148; 8,174,395; and 8,461,997, which are hereby incorporated by reference in their entireties for their teachings related to wireless transmission arrangements between sensor guide wires and physiological monitors, and the structure and use of sensor guide wire devices.

The sensor element 108 may be used to sense any suitable physiological variable, such as, for example, pressure or temperature or flow. The sensor may be a microchip, a pressure sensitive device in the form of a membrane, a thermistor, a sensor for measuring the concentration or presence of a blood analyte, or other suitable pressure, temperature, or other variable-measuring device. Furthermore, the sensor element 108 may be a plurality of sensor devices. The physiological monitor 130 may use the sensor readings from the sensor element 108 to determine blood pressure, blood temperature, blood flow, the concentration or presence of one or more blood analytes, and/or Fractional Flow Reserve measurements (FFR) or other pressure relationships. In short, FFR is used to identify constrictions of coronary vessels by obtaining the ratio between the pressures distally and proximally of a constriction.

Figure 2:
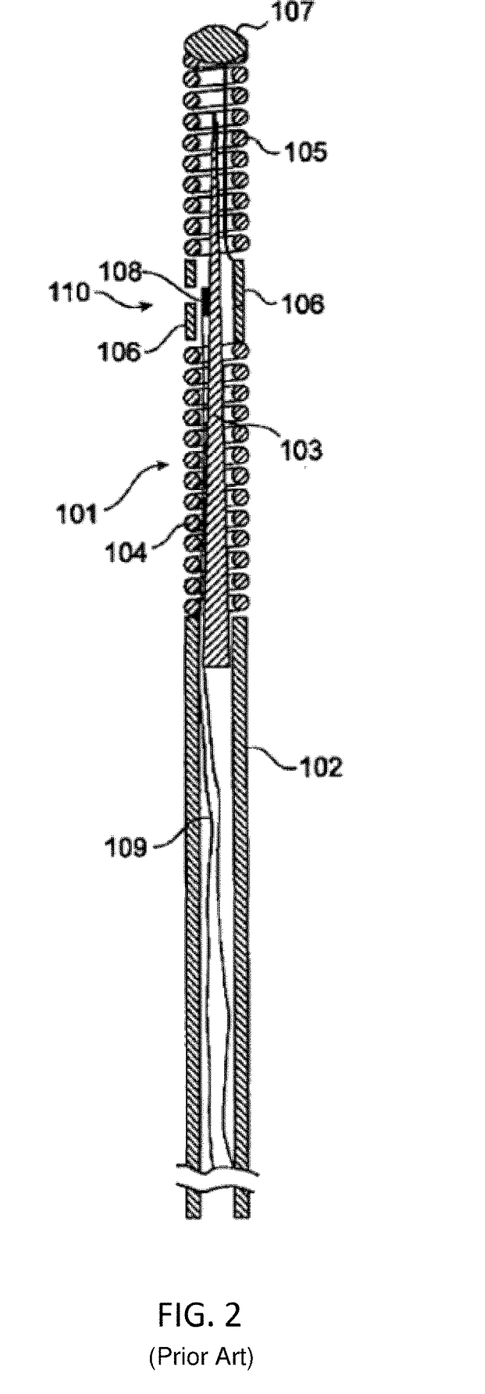
FIG. 2 shows an exemplifying sensor mounted on a guide wire that may be used in the system of FIG. 1.

FIG. 2 illustrates an exemplifying sensor mounted on a guide wire (as described in U.S. Pat. No. 8,698,638, which is hereby incorporated by reference in its entirety for the devices and methods disclosed therein related to guide wires) that may be used in the system of FIG. 1. The sensor guide wire 101 comprises a hollow tube 102, a core wire 103, a first coil 104, a second coil 105, a jacket or sleeve 106, a dome-shaped tip 107, a sensor element or chip 108, and one or several electrical leads 109. The hollow tube 102 has typically been treated to give the sensor guide construction a smooth outer surface with low friction. The proximal end of the first coil 104 is attached to the distal end of the hollow tube 102, while the distal end of the first coil 104 is attached to the proximal end of the jacket 106. The proximal end of the second coil 105 is connected to the distal end of the jacket 106, and the dome-shaped tip 107 is attached to the distal end of the second coil 105. The core wire 103 is at least partly disposed inside the hollow tube 102 such that the distal portion of the core wire 103 extends out of the hollow tube 102 and into the second coil 105. The sensor element 108 is mounted on the core wire 103 at the position of the jacket 106, and is connected to an external physiology monitor (e.g., the physiological monitor 130 of FIG. 1) via the electrical leads 109. The sensor element 108 comprises a pressure sensitive device in the form of a membrane (not shown in FIG. 2), which through an aperture 110 in the jacket 106 is in contact with a medium, such as blood, surrounding the distal portion of the sensor guide wire 101.

SUMMARY

In conventional guide wires, the core wire is cylindrical and provides favorable torque transmission around a bend. However, the cylindrical core wire has no preferential bending plane, which can lead to the formation of a spiral shape in the tip resulting in poor tip durability.

Thus, there is a need for an improved sensor guide wire having a core wire including a flattened portion to provide a preferential bending plane that improves re-shapeability, and lowers the cross-sectional area moment of inertia, which in turn reduces a force required to buckle the tip and improves a tip durability by reducing the stresses experienced during bending.

In one embodiment, a guide wire includes a core wire having a flattened portion configured to preferentially bend the core wire in at least one plane that passes through a longitudinal axis of the core wire. A distal most end of the flattened portion is spaced from a distal most end of the core wire.

In another embodiment, a sensor guide wire for an intravascular measurement of a physiological variable in a living body includes a sensor element configured to measure the physiological variable, a coil, and a core wire at least partially disposed within the coil. The portion of the core wire disposed within the coil includes a flattened portion configured to allow the core wire to preferentially bend in at least one plane that passes through a longitudinal axis of the core wire. A distal most end of the flattened portion is spaced from a distal most end of the core wire.

All documents cited in this disclosure are hereby incorporated by reference in their entireties for the devices, techniques, and methods described therein relating to medical sensors and devices, and for any disclosure relating to medical sensors and devices.

BRIEF DESCRIPTION OF THE DRAWINGS

The features, aspects and advantages of the present invention will become apparent from the following description, appended claims, and the accompanying exemplary embodiments shown in the drawings, which are briefly described below.

DETAILED DESCRIPTION

Before turning to the figures, which illustrate the exemplary embodiments in detail, it should be understood that the present invention is not limited to the details or methodology set forth in the description or illustrated in the figures.

FIGS. 3-8 illustrate preferred embodiments of the invention that can be used instead of the core wire 103 of FIG. 2. A sensor mounted on a guide wire including the core wire illustrated in FIGS. 3-8 may be used, for example, in the system of FIG. 1.

The sensor element 108 is connected to the microcables or optical signal lines 109, for transmitting signals between the sensor element 108 in the distal part of the guide wire and the connector 112 at the proximal end of the hollow tube 102. Examples of suitable microcables are described, for example, in U.S. Patent Application Publication No. 2010/0228112, U.S. Patent Application Publication No. 2011/0213220, and U.S. Patent Application Publication No. 2012/0289808, all of which are hereby incorporated by reference in their entireties for their teachings related to microcables in guide wire assemblies and the structure and use of guide wire assemblies.

The diameter of the sensor guide wire 101 preferably varies between about 0.25 to about 2.5 mm; for use in coronary arteries, for example, the diameter is normally about 0.35 mm. In the context of length, width, diametrical, and other spatial dimensions, the modifier "about" can include a deviation of plus or minus 0 to 10% of the amount it modifies, preferably plus or minus 0 to 5% of the amount it modifies.

Referring to FIGS. 3-6, a portion of the core wire 208 including a flattened portion 208B (which will be described below) is disposed within a coil 206 at the distal end of the sensor guide wire 101. However, as seen in the figures, the flattened portion is not provided at the distal most end of the core wire 208. Instead, a distal most end of the flattened portion 208B is spaced from a distal most end of the core wire 208, for example, by a length of a portion 208A (described in further detail below). The core wire 208 may be made out of stainless steel, nitinol, or cobalt chromium. The core wire 208 may be made by grinding. The geometry of the core wire illustrated in FIGS. 3-6 is the geometry of the core wire 208 prior to being shaped by a surgeon.

Figure 3:
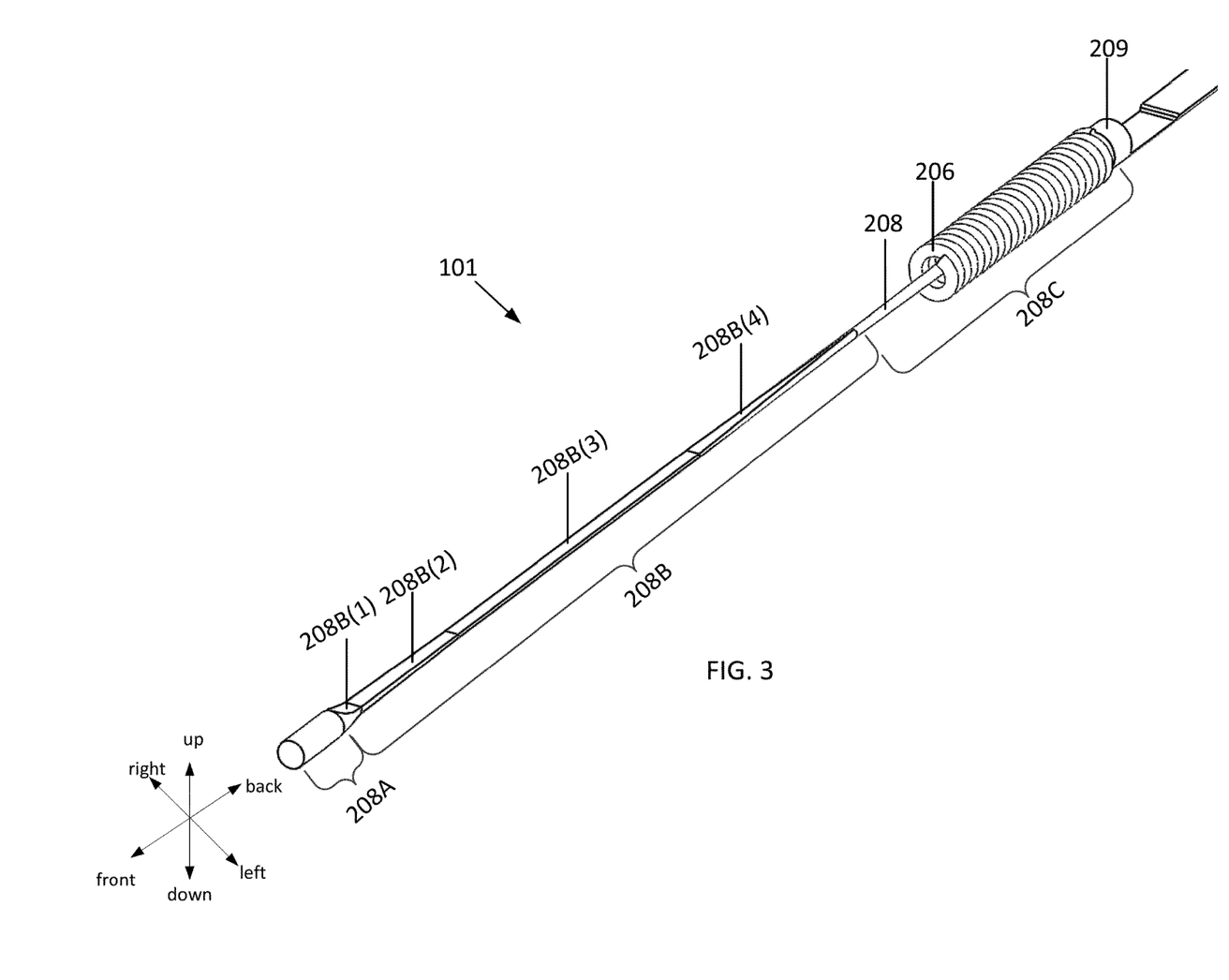
FIG. 3 is an isometric view of a distal end of a sensor guide wire according to one embodiment of the invention, where a core wire includes a flattened portion.

As seen in the legend provided in FIG. 3, the sensor guide wire 101 and the core wire 208 can be move along three axes, namely, in a front-back direction, an up-down direction, and a right-left direction. The sensor guide wire 101 and the core wire 208 can also be rotated.

Referring to FIG. 3, the core wire 208 is disposed within the coil 206. The coil 206 may extend to a distal tip such as the dome-shaped tip 107 seen in FIG. 2, but the distal portion of the coil 206 has been removed from FIG. 3 for clarity. The coil 206 corresponds to the second coil 105 of FIG. 2. The portion of the core wire 208 disposed within the coil 206 may comprise a first portion 208A at a distal end portion, a second portion 208B proximal to the first portion 208A, and a third portion 208C proximal to the second portion 208B. The first portion 208A (i.e., the distal most end portion) of the core wire 208 may serve as a weld paddle. The second portion 208B is the flattened portion of the core wire 208. As used herein, the term "flattened portion" refers to a portion of the core wire having at least one planar surface (and sometimes two or more planar surfaces). The second portion 208B is not twisted.

A length (in the front-back direction) of the first portion 208A, the second portion 208B, and the third portion 208C may be, for example, approximately 0.2 mm to 1 mm, 5 mm to 15 mm, and 15 to 25 mm, respectively. In one example, a length (in the front-back direction) of the first portion 208A, the second portion 208B, and the third portion 208C may be 0.5 mm, 15 mm to 16.5 mm, and 13 mm, respectively. It may be preferable to make the first portion 208A as small as possible. In another example, the second portion 208B (i.e., the flattened portion) is approximately half the length of the portion stretching from the first portion 208A to a connector portion 209. As illustrated in FIGS. 3-6, the second portion 208B is the portion of the core wire 208 having the greatest length, followed by, in order of decreasing length, the third portion 208C and the first portion 208A. However, in other embodiments, the length of each portion with respect to the remaining portions can be altered in order to change the overall mechanical properties, such as flexibility, torqueability and pushability, of the sensor guide wire 101.

The portions 208A-208C of the core wire 208 may be connected (e.g., by welding), integrally formed or a combination thereof. In one embodiment, the core wire 208 (i.e., the first portion 208A, the second portion 208B and the third portion 208C) may be integrally formed from a single piece (e.g., a single piece of metal). In other words, from the first portion 208A to the connector portion 209, the core wire 208 is formed of the same material. In another embodiment, the core wire 208 may be formed from at least two pieces (e.g., multiple pieces of metal). In the embodiments in which the core wire 208 is formed from multiple pieces of metal, each of the first portion 208A, the second portion 208B and the third portion 208C may be formed of the same metal or of different types of metal with respect to one another. In addition, each of the first portion 208A, the second portion 208B and the third portion 208C may be individually formed from a separate piece of metal. Alternatively, two of the first portion 208A, the second portion 208B and the third portion 208C may be formed from one piece of metal, while the remaining portion is formed from a separate piece of metal.

The core wire 208 may optionally include a connector portion 209 configured to connect with the jacket or sleeve 106. In embodiments in which the sensor guide wire does not include a jacket or sleeve 106, the connector portion 209 may connect to a braided portion or the hollow tube 102 (if a braided portion is not provided). As discussed above, the core wire 208 may be longer than the hollow tube 102, and may extend from a proximal connector, through the jacket or sleeve 106, and to the dome-shaped tip 107 of the sensor guide wire 101. In other words, the portion of the core wire illustrated in FIGS. 3-6 may be the portion of the core wire present within the coil 206. The overall length of the core wire 208 is illustrated, for example, in FIG. 7A. In FIG. 3, one or more sensor elements 108 (not shown) are mounted just proximal of the connector portion 209. For example, the sensor element 108 may be mounted in a chip pocket 210 of FIGS. 7A and 8.

Figure 9:
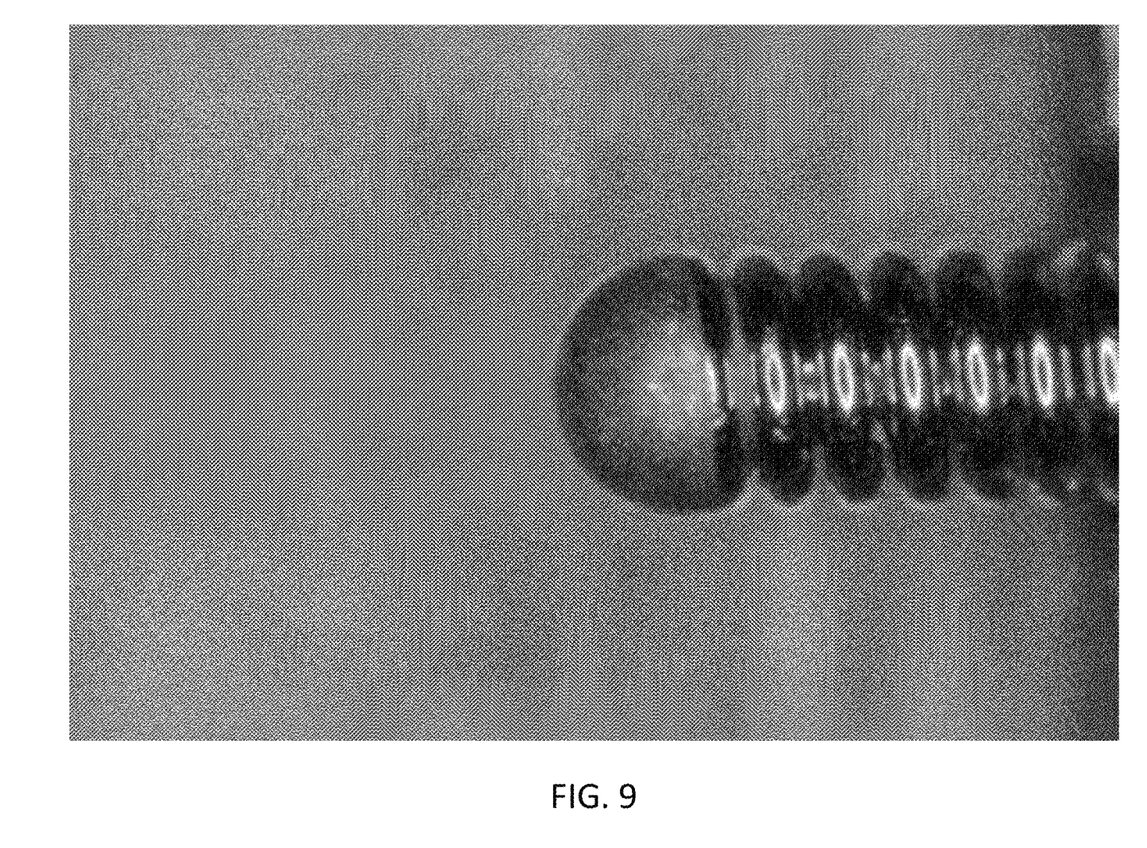
FIG. 9 illustrates the distal most end of the core wire of FIG. 3 thermally welded to the coil of FIG. 3.

The first portion 208A is the portion located at the distal most end of the core wire 208. In one embodiment, the coil 206 is attached to the core wire 208 by thermal welding the first portion 208A to the coil 206 (see FIG. 9). For example, the first portion 208A and the coil 206 may be melded together by laser or plasma welding. No solder is added, thereby increasing the ease of manufacturing by decreasing the amount of material required. Because the core wire 208 is thermally welded to the coil 206 without the addition of solder, a distal most end of the flattened portion 208B is spaced from a distal most end of the core wire 208, for example, by a distance equal to the length of the first portion 208A (which may be, for example, 0.5 mm, 1.0 mm, 1.5 mm or 2.0 mm). Providing such a spacing between the distal most end of the flattened portion 208B and the distal most end of the core wire 208 provides enough core wire material to be thermally welded to the coil, without impacting the strength of the flattened portion 208B or the rest of the core wire 208. As seen in FIG. 9, the distal most end of the core wire 208 becomes spherical when thermally welded to the coil 206.

Figure 4A:
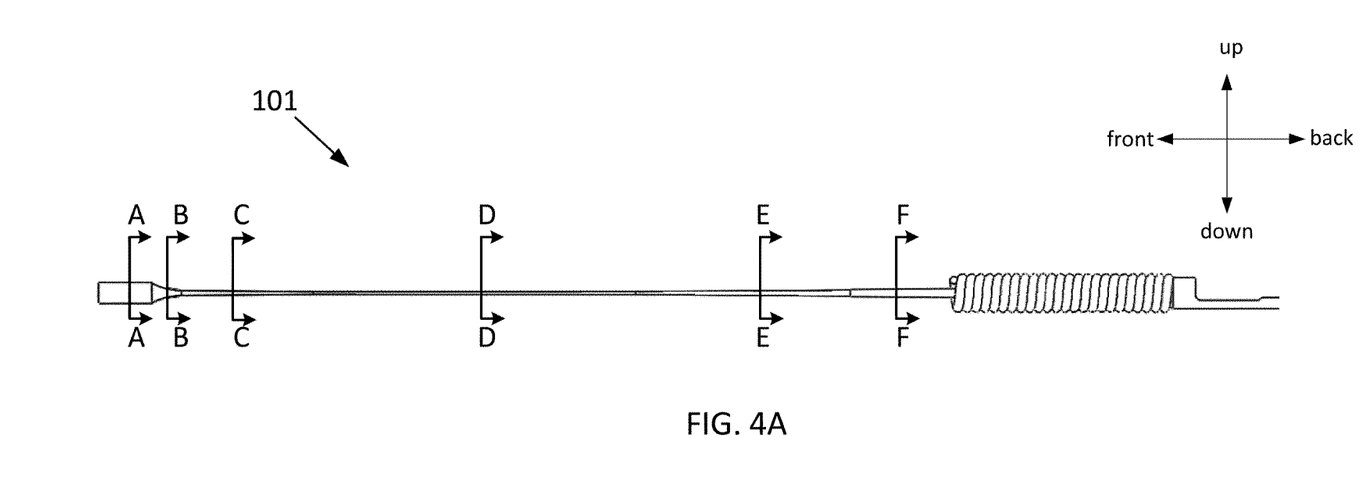
FIG. 4A is a side view of the core wire and coil of FIG. 3.
Figure 4B:
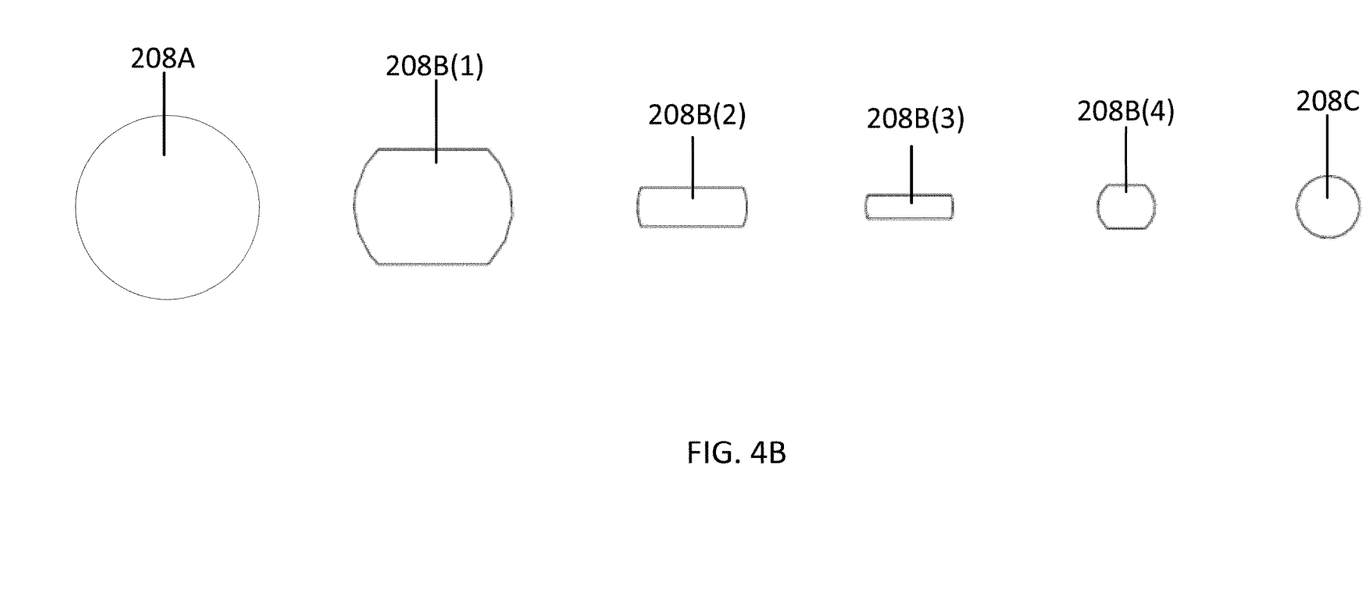
FIG. 4B illustrates the cross-sections of the portions of the core wire taken through the lines A-A, B-B, C-C, D-D, E-E, and F-F of FIG. 4A.

In one embodiment, the first portion 208A, the second portion 208B and the third portion 208C have the cross-sections illustrated in FIG. 4B. As seen in FIG. 4B, the first portion 208A and the third portion 208C are rounded (i.e., have a circular or ovular cross-section). The second portion 208B (i.e., the flattened portion of the core wire 208) includes a first flattened portion 208B(1) at a distal end of the flattened portion 208B, a second flattened portion 208B(2) proximal to the first flattened portion 208B(1), a third flattened portion 208B(3) proximal to the second flattened portion 208B(2), and a fourth flattened portion 208B(4) proximal to the third flattened portion 208B(3).

In one embodiment, the first flattened portion 208B(1), the second flattened portion 208B(2), the third flattened portion 208B(3) and the fourth flattened portion 208B(4) may be integrally formed from a single piece (e.g., a single piece of metal). In another embodiment, the first flattened portion 208B(1), the second flattened portion 208B(2), the third flattened portion 208B(3) and the fourth flattened portion 208B(4) may be formed from at least two pieces (e.g., multiple pieces of metal). In the embodiments in which the first flattened portion 208B(1), the second flattened portion 208B(2), the third flattened portion 208B(3) and the fourth flattened portion 208B(4) are formed from multiple pieces of metal, each of the first flattened portion 208B(1), the second flattened portion 208B(2), the third flattened portion 208B(3) and the fourth flattened portion 208B(4) may be formed of the same metal or of different types of metal with respect to one another. In addition, each of the first flattened portion 208B(1), the second flattened portion 208B(2), the third flattened portion 208B(3) and the fourth flattened portion 208B(4) may be individually formed from a separate piece of metal. Alternatively, the first flattened portion 208B(1), the second flattened portion 208B(2), the third flattened portion 208B(3) and the fourth flattened portion 208B(4) may be formed from one piece of metal, while the remaining flattened portion(s) is formed from at least one separate piece of metal.

A length (in the front-back direction) of the first flattened portion 208B(1), the second flattened portion 208B(2), the third flattened portion 208B(3) and the fourth flattened portion 208B(4) may be, for example, approximately 0.1 mm to 1 mm, 0.5 mm to 3 mm, 3 mm to 13 mm, and 0.5 mm to 3 mm, respectively. In one example, a length (in the front-back direction) of the first flattened portion 208B(1), the second flattened portion 208B(2), the third flattened portion 208B(3) and the fourth flattened portion 208B(4) may be 0.3 mm, 1.5 mm, 13 mm, and 2 mm, respectively. The third flattened portion 208B(3) is longer than the first flattened portion 208B(1), the second flattened portion 208B(2) and the fourth flattened portion 208B(4). The second flattened portion 208B(2) may have, for example, a length of 1.5 mm, a width (in the right-left direction) of 0.05 mm to 0.15 mm, and a height (in the up-down direction) of 0.01 mm to 0.05 mm. The third flattened portion 208B(3) may have, for example, a length of 13 mm, a width (in the right-left direction) of 0.09 mm, and a height (in the up-down direction) of 0.025 mm.

As seen in FIGS. 3 and 4, the first flattened portion 208B(1) and the second flattened portion 208B(2) are round to flat transition portions disposed between the rounded first portion 208A and the third flattened portion 208B(3), which has a substantially constant rectangular or square cross-section. The third flattened portion 208B(3) is planar prior to being shaped by a surgeon. The fourth flattened portion 208B(4) is a flat to round transition portion disposed between and the third flattened portion 208B(3) and the rounded third portion 208C.

Figure 5A:
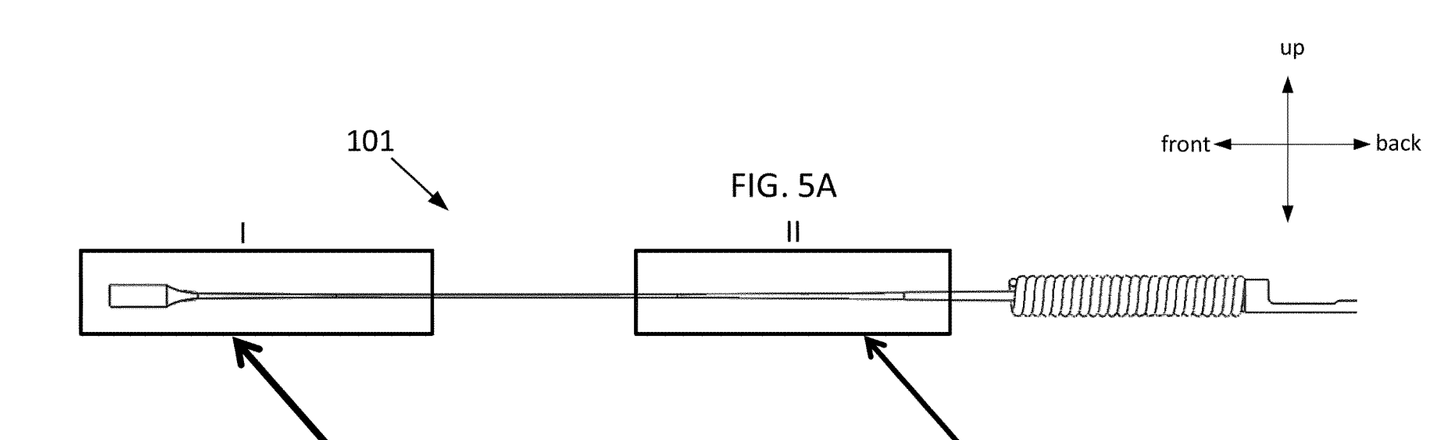
FIG. 5A is another side view of the core wire and coil of FIG. 3.
Figure 5B:
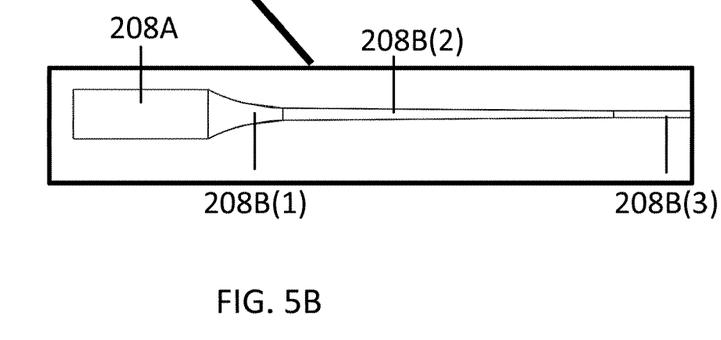
FIG. 5B is an enlarged side view of the section I of FIG. 5A.
Figure 5C:
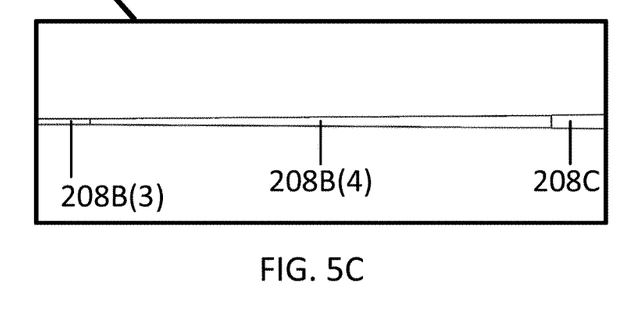
FIG. 5C is an enlarged side view of the section II of FIG. 5A.
Figure 6:
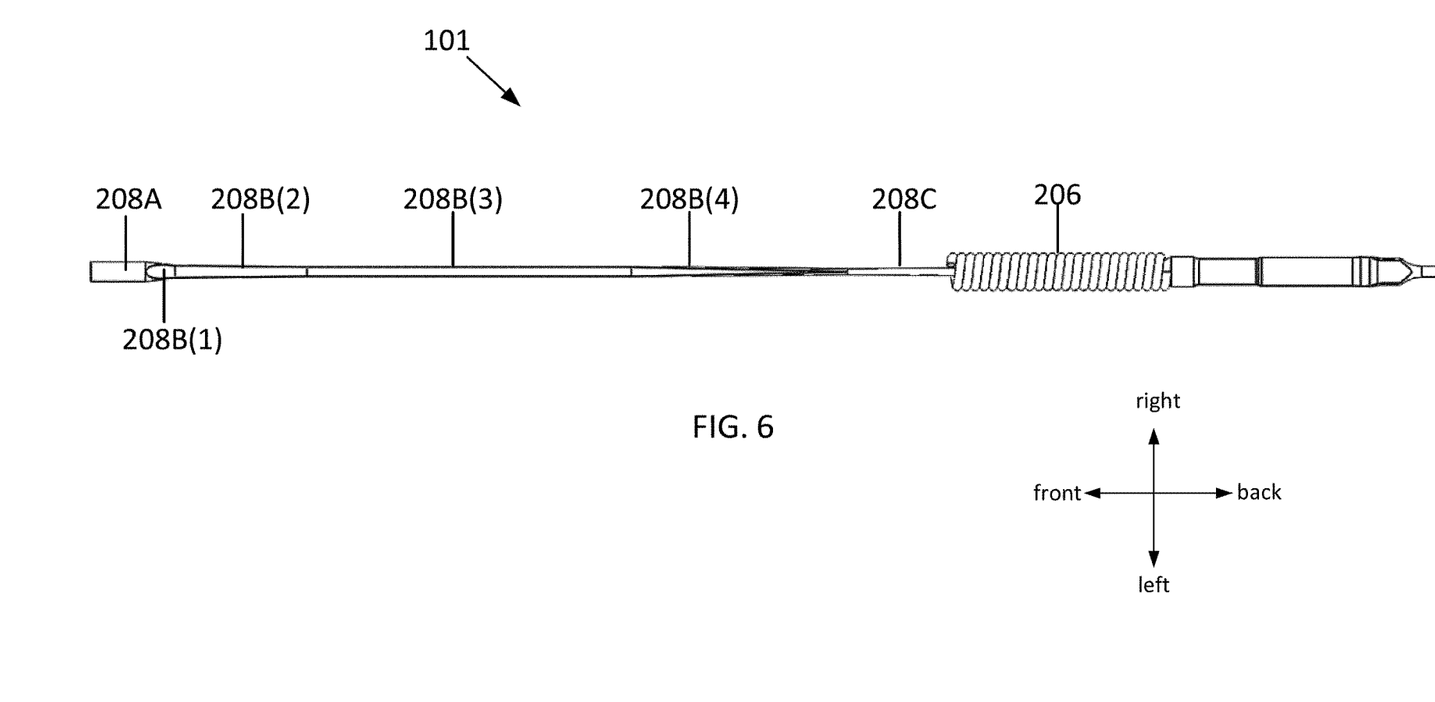
FIG. 6 is a top view of the core wire and coil of FIG. 3.
Figure 7A:
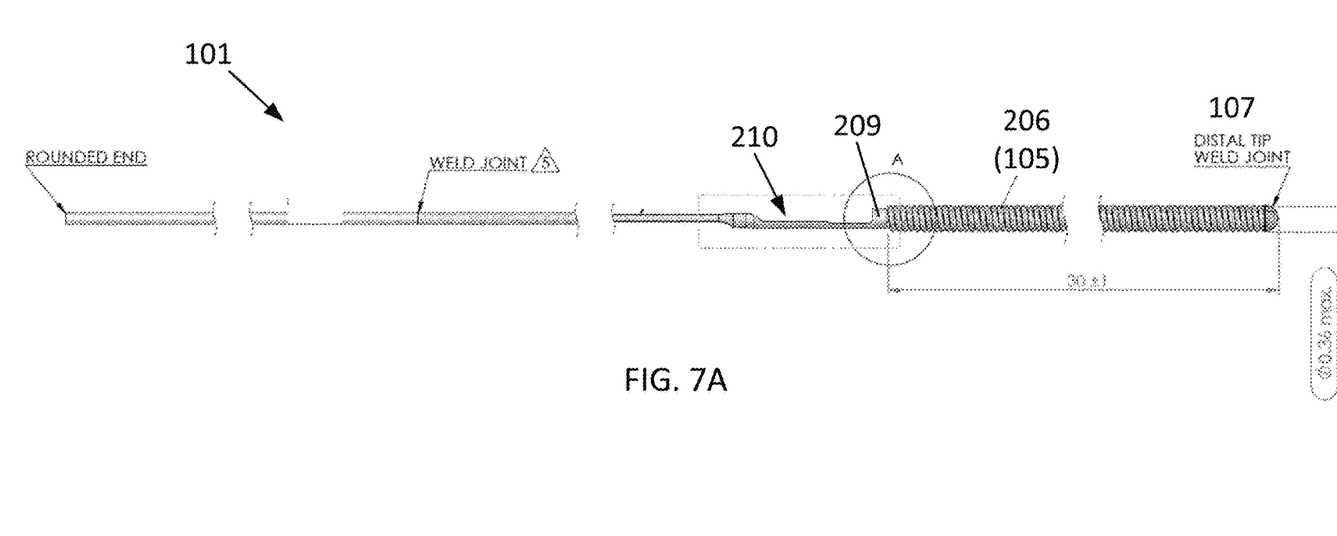
FIG. 7A is a side view of an overall length of the core wire of FIG. 3.
Figure 7B:
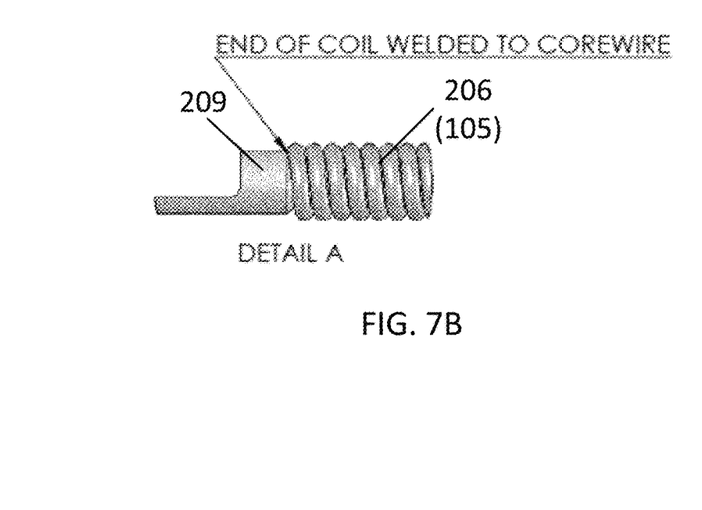
FIG. 7B is an enlarged side view of the Detail A of FIG. 7A.

As seen in FIG. 5B, from the first portion 208A (located proximate to the dome-shaped tip 107) to the third flattened portion 208B(3), the cross-sectional area of the core wire 208 decreases and the core wire 208 becomes progressively more flat. As seen in FIG. 5C, from the third flattened portion 208B(3), the cross-sectional area of the core wire 208 increases and the core wire 208 because progressively more round.

As seen in FIG. 4B, the cross-section of each of the first portion 208A, the second portion 208B (including the flattened portions 208B(1)-208B(4)), and the third portion 208C are symmetrical with respect to at least one plane that passes through the longitudinal axis of the core wire 208.

As discussed in the Background section, the sensor guide wire 101 has to be steered often several feet into a patient, for example, from an opening in the femoral artery in the leg of the patient up to the heart through tortuous blood vessels. The mechanical characteristics (such as maneuverability, steerability, torqueability, and pushability) of a sensor guide wire 101 are very important to a surgeon because the surgeon grasps the proximal end of the sensor guide wire 101 (sticking outside the patient), and by manipulating the proximal end, steers the distal end of the sensor guide wire 101, which is often several feet away, in the front-back direction, the up-down direction, and the right-left direction in order to reach its target (e.g., the heart). Because the distal end of the sensor guide wire 101 is going to be inserted furthest into the patient, it is desirable to make the distal end of the sensor guide wire 101 as flexible as possible so that the sensor guide wire 101 can be easily and predictably maneuvered in a tortuous path.

Because the core wire 208 includes the straight and flat portion 208B(3), it is relatively easy to maneuver the core wire 208 in the front-back direction and the up-down direction by manipulating the proximal end of the sensor guide wire. However, it is more difficult to maneuver the core wire 208 in the right-left direction by manipulating the proximal end of the sensor guide wire because the core wire 208 is stiffer in the right-left direction than in the up-down direction. In other words, there is preferential movement in the up-down direction, as compared to the right-left direction. As a result, the core wire 208 exhibits preferential bending in a plane extending along the up-down direction. In some embodiments, the core wire 208 exhibits preferential bending in the up direction to the same degree as the core wire 208 exhibits preferential bending in the down direction. This preferential bending allows a physician to bend the sensor guide wire 101, in particular, the core wire 208 in a predictable direction. In particular, torque supplied to the proximal end of the core wire 208 is transmitted along the length of the core wire 208 and enables the core wire 208, in particular, the flattened portion 208B (which may be shaped) to be easily reoriented to point in the desired direction. Moreover, the core wire 208 resists bending in the right-left direction, thereby allowing the surgeon to more easily route the core wire 208 to the target. The flattened portion 208B improves re-shapeability by providing a consistent and preferential bending plane. In addition, the flattened portion 208B allows the sensor guide wire 101 to retain less permanent deformation when subjected to bending conditions. The flattened portion 208B also lowers the cross-sectional area moment of inertia, which in turn reduces the force to buckle the dome-shaped tip 107 and improves the durability of the dome-shaped tip 107 by reducing the stresses experienced during bending.

In the embodiments of FIGS. 3-6, the core wire 208 includes both a round proximal portion (i.e., the third portion 208C) and a flattened portion (i.e., the second portion 208B) that is distal to the third portion 208C. The round proximal portion provides a certain level of stiffness for steerability in tortuous anatomies and the flattened portion provides a shaping region where the physician can manipulate the core wire to preferentially bend in an up-down direction in curves or bends to meet the needs of the use scenario.

Figure 8:
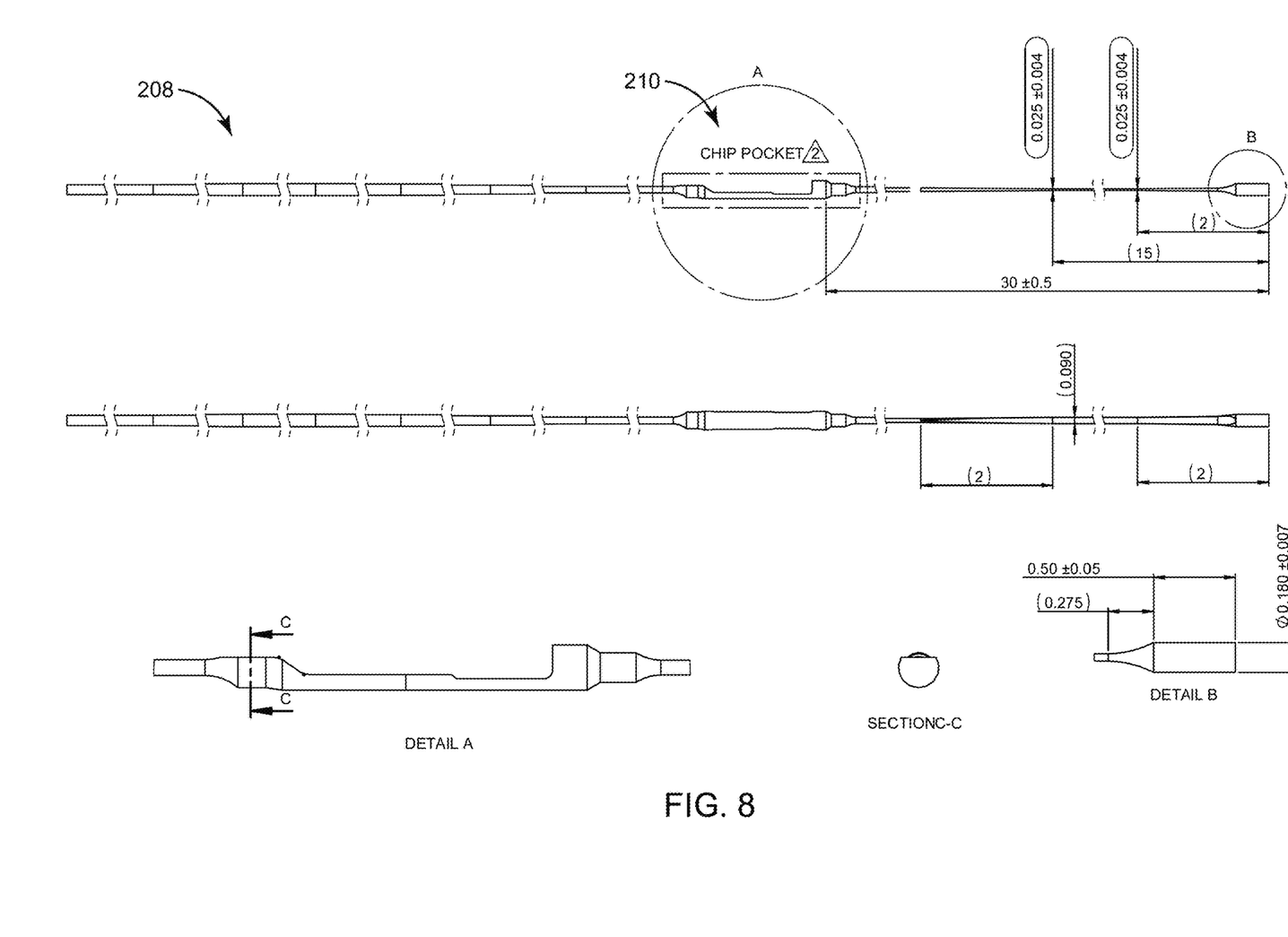
FIG. 8 illustrates the core wire of FIG. 3 including exemplary dimensions.

FIG. 8 illustrates an example of the sensor guide wire 101 described in the embodiments above, including illustrative dimensions having units of millimeters.

Although not illustrated, the core wire 208 may have different configurations, provided that the core wire 208 includes at least one flattened portion (or other shape that has a preferential bending direction, such as an elongated ellipse). For example, the entire core wire 208 may be flat. In another example, the core wire 208 may include a flattened portion and at least one rounded portion. As used herein, the term "rounded portion" refers to a portion of the core wire having a circular or ovular cross-section. In other words, the rounded portion of the core wire does not include any flattened portions.

In yet another example, the core wire 208 may include a first rounded portion (e.g., the first portion 208A), a second rounded portion (e.g., the third portion 208C), and a flattened portion (e.g., the second portion 208B) provided between the first rounded portion and the second rounded portion. In another example, the core wire 208 may include a plurality of flattened portions and at least one rounded portion. A first flattened portion may have the same dimensions as a second flattened portion, or the first flattened portion may have different dimensions from the second flattened portion. The first flattened portion and the second flattened portion may be immediately adjacent to each other or the first flattened portion and the second flattened portion may be separated by at least one rounded portion. In other embodiments, the core wire 208 may include more than two flattened portions.

The core wire 208 may have more than three portions, or the core wire 208 may have fewer than three portions. For example, the first portion 208A and/or the third portion 208C may be omitted. In the case where the third portion 208C is omitted, the proximal end of the second portion 208B may directly connect to the connector portion 209 or extend to and mate with the jacket or sleeve 106. Any portion except for the second portion 208B (i.e., the flattened portion) may be omitted. In addition, as discussed above, additional flattened and rounded portions may be added.

In some embodiments, the entire core wire 208 may be flat (i.e., the core wire 208 may consist of only the flattened portion 208B).

The core wire described in any of the embodiments may also be used with a guide wire without a sensor or a guide wire with or without a braided portion. The core wire described in any of the embodiments may also be used with a guide wire without a coil.

The construction and arrangements of the core wire, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. Other substitutions, modifications, changes and omissions may also be made in the design, operating conditions and arrangement of the various exemplary embodiments without departing from the scope of the present invention. Features of one embodiment may be combined with a feature of another embodiment.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise form provided. Accordingly, these terms should be interpreted as indicating that insubstantial or inconsequential modifications or alterations of the subject matter described and claimed are considered to be within the scope of the invention.

What is claimed is:

1. A guide wire configured for intravascular insertion, the guide wire comprising:
a core wire (208) comprising, in a direction from a distal end of the core wire (208) to a proximal end of the core wire (208):
a first portion (208A) that is located at a distal-most end of the core wire (208), wherein the first portion (208A) has a circular or ovular cross-section,
a second portion (208B) configured to allow the core wire (208) to preferentially bend in at least one plane that passes through a longitudinal axis of the core wire (208), wherein the second portion (208B) comprises:
a first flattened portion (208B(1)) that extends proximally from the first portion (208A), wherein the first flattened portion (208B(1)) is a round-to-flat transition portion,
a second flattened portion (208B(2)) that extends proximally from the first flattened portion (208B(1)), wherein the second flattened portion (208B(2)) becomes progressively more flat from a distal end of the second flattened portion (208B(2)) to a proximal end of the second flattened portion (208B(2)), and wherein a cross-sectional area of the core wire (208) at the distal end of the second flattened portion (208B(2)) is less than a cross-sectional area of the core wire (208) at a proximal end of the first portion (208A),
a third flattened portion (208B(3)) that is located directly adjacent to the second flattened portion (208B(2)) and extends proximally from the second flattened portion (208B(2)), wherein the third flattened portion (208B(3)) has a substantially constant cross-section, and wherein a cross-sectional area of the core wire (208) at a distal end of the third flattened portion (208B(3)) is less than a cross-sectional area of the core wire (208) at the distal end of the second flattened portion (208B(2)),
a fourth flattened portion (208B(4)) that is located directly adjacent to the third flattened portion (208B(3)) and extends proximally from the third flattened portion (208B(3)), wherein the fourth flattened portion (208B(4)) is a flat-to-round transition portion, and a third portion (208C) that is located directly adjacent to the fourth flattened portion (208B(4)) and extends proximally from the fourth flattened portion (208B(4)), wherein the third portion (208C) has a circular or ovular cross-section.

2. The guide wire of claim 1, wherein a cross-sectional area of the core wire (208) at a distal end of the third portion is greater than a cross-sectional area of the core wire (208) at a proximal end of the third flattened portion (208B(3)).

3. The guide wire of claim 1, wherein an overall length of the second and third flattened portions (208B(2), 208B(3)) is greater than a length of the first portion and greater than a length of the third portion.

4. The guide wire of claim 1, wherein a cross-section of each of the first portion (208A), the second portion (208B), and the third portion (208C) is symmetrical with respect to at least one plane that passes through and extends along the longitudinal axis of the core wire (208).

5. The guide wire of claim 1, wherein the first portion (208A), the second portion (208B), and the third portion (208C) are integrally formed from a single piece.

6. The guide wire of claim 1, wherein an overall length of the second and third flattened portions (208B(2), (208B(3)) is greater than a length of the first flattened portion (208B(1)) and greater than a length of the fourth flattened portion (208B(4)).

7. The guide wire of claim 1, wherein each of the second flattened portion (208B(2)) and the third flattened portion (208B(3)) has an approximately rectangular cross-section.

8. The guide wire of claim 1, wherein the core wire (208) is configured to preferentially bend in a plane that passes through the longitudinal axis of the core wire (208) and extends in an up-down direction of the core wire (208).

9. The guide wire of claim 8, wherein the core wire (208) is configured to preferentially bend in an up direction to a same degree as the core wire (208) is configured to preferentially bend in a down direction.

10. The guide wire of claim 1, wherein the second and third flattened portions (208B(2), 208B(3)) are not twisted.

11. The guide wire of claim 1, further comprising:
a sensor element configured to measure a physiological variable in a living body; and
a coil (206),
wherein a portion of the core wire (208) is disposed within the coil (206).

12. The guide wire of claim 11, wherein at least a portion of the third flattened portion (208B(3)) is disposed within the coil (206).

13. The guide wire of claim 11, further comprising a jacket (106) proximal to the coil (206), wherein the coil (206) is attached to an inner circumference or an outer circumference of the jacket (106).

14. The guide wire of claim 13, wherein the portion of the core wire (208) disposed within the coil (206) further comprises a connector portion (207) configured to mate with a distal end of the jacket (106).

15. The guide wire of claim 1, wherein the core wire (208) is made out of stainless steel, nitinol, or cobalt chromium.

16. The guide wire of claim 1, wherein the first portion (208A) has a circular cross-section.

17. The guide wire of claim 1, wherein the third portion (208C) has a circular cross-section.

18. The guide wire of claim 1, wherein:
the first flattened portion (208B(1)) is located directly adjacent to the first portion (208A), and
the second flattened portion (208B(2)) is located directly adjacent to the first flattened portion (208B(1)).

19. The guide wire of claim 1, wherein, in a cross-sectional view of the first flattened portion (208B(1)), the first flattened portion (208B(1)) has two opposing rounded sides and two opposing flat sides.

20. The guide wire of claim 1, wherein, in a cross-sectional view of the fourth flattened portion (208B(4)), the fourth flattened portion (208B(4)) has two opposing rounded sides and two opposing flat sides.

21. The guide wire of claim 1, wherein:
in a cross-sectional view of the second flattened portion (208B(2)), the second flattened portion (208B(2)) has two opposing rounded sides and two opposing flat sides, and
in a cross-sectional view of the third flattened portion (208B(3)), the third flattened portion (208B(3)) has two opposing rounded sides and two opposing flat sides.

22. The guide wire of claim 1, wherein:
a length of the first portion (208A) is in a range of 0.2 mm to 1 mm,
a length of the first flattened portion (208B(1)) is in a range of 0.1 mm to 1 mm,
a length of the second flattened portion (208B(2)) is in a range of 0.5 mm to 3 mm,
a length of the third flattened portion (208B(3)) is in a range of 3 mm to 13 mm,
a length of the fourth flattened portion (208B(4)) is in a range of 0.5 mm to 3 mm, and
a length of the third portion (208C) is in a range of 15 mm to 25 mm.

23. The guide wire of claim 1, wherein a height of the second flattened portion (208B(2)) in a direction between flat surfaces of the second flattened portion (208B(2)) is in a range of 0.01 mm to 0.05 mm.

24. The guide wire of claim 23, wherein a height of the third flattened portion (208B(3)) in a direction between flat surfaces of the third flattened portion (208B(3)) is 0.025 mm.

25. The guide wire of claim 1, wherein:
a width of the second flattened portion (208B(2)) in a direction perpendicular to a direction between flat surfaces of the second flattened portion (208B(2)) is greater than a width of the third flattened portion (208B(3)) in a direction perpendicular to a direction between flat surfaces of the third flattened portion (208B(3)).

* * * * *